United States Patent [19]

Tashiro et al.

[11] 4,224,239
[45] Sep. 23, 1980

[54] PROCESS FOR PREPARING OPTICALLY ACTIVE AMINO ACID OR MANDELIC ACID

[75] Inventors: Yasuhisa Tashiro, Yokohama; Takashi Nagashima, Saitama; Shigeru Aoki; Rinzo Nishizawa, both of Tokyo, all of Japan

[73] Assignee: Nippon Kayaku Kabushiki Kaisha, Tokyo, Japan

[21] Appl. No.: 33,021

[22] Filed: Apr. 24, 1979

Related U.S. Application Data

[62] Division of Ser. No. 886,745, Mar. 15, 1978.

[30] Foreign Application Priority Data

Mar. 24, 1977 [JP] Japan ................................. 52/31555

[51] Int. Cl.² .................. C07C 101/04; C07C 101/08; C07B 19/00
[52] U.S. Cl. ........................... 260/501.11; 260/501.12; 562/401; 562/402
[58] Field of Search ............... 562/401, 402, 470, 575, 562/559; 260/501.11, 501.12

[56] References Cited

U.S. PATENT DOCUMENTS

| | | | |
|---|---|---|---|
| 2,820,827 | 1/1958 | Ruschig et al. | 562/401 X |
| 3,897,484 | 7/1975 | Asai et al. | 562/575 X |
| 3,976,680 | 8/1976 | Clark et al. | 562/559 X |

*Primary Examiner*—Natalie Trousof
*Assistant Examiner*—Vera C. Clarke
*Attorney, Agent, or Firm*—Stevens, Davis, Miller & Mosher

[57] ABSTRACT

Two optically active amino acid-mandelic acid complexes are obtained by interacting in a solvent under pH conditions of 1.0–4.0 an amino acid expressed by a general formula

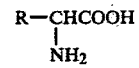

(in which R represents a methyl group, an ethyl group or a methylthioethyl group) and mandelic acid, one of the acids being an optically active substance and the other being a racemic modification, and optically resolving the resulting complexes into two diastereoisomers by using solubility difference therebetween. The optically active complexes are each decomposed by means of an acid, a strongly acidic ion-exchange resin, or a weakly basis ion-exchange resin to obtain optically active amino acids or optically active mandelic acid.

9 Claims, No Drawings

PROCESS FOR PREPARING OPTICALLY ACTIVE AMINO ACID OR MANDELIC ACID

This is a division of application Ser. No. 886,745, filed Mar. 15, 1978.

This invention relates to novel optically active amino acid-mandelic acid complexes and a process for preparing such complexes. The present invention is also concerned with a process for preparing optically active amino acids or mandelic acid by decomposition of the complexes.

As well known, the optical resolution of amino acid can be broadly classified into the following three categories.

1. A chemicophysical method including a natural resolution, an asymmetric crystallization or the like.
2. An asymmetric hydrolysis using enzymes.
3. A method using optically active resolving agents.

Typical of the chemicophysical resolution method (1) are: a method for preparing alanine in which alanine in the form of a benzenesulfonate is optically resolved (Bull. Agr. Chem. Soc. Japan, 22, 218 (1958)); and a method for preparing optically active methionine in which methionine is treated by the successive steps of N-acylation, conversion into an ammonium salt, optical resolution and deacetylation (Japanese Patent Publication No. 39-24440). However, these methods are disadvantageous in that since the amount of production of optically active compounds in one batch is very small, an apparatus of large scale is required industrially, incurring great expense for installation of such apparatus.

Specific examples of the resolution method (2) using enzymes are: a method for preparing optically active alanine in which acylated alanine is resolved by the use of aminoacylase (J. Biol. Chem. 194, 455 (1955)); a method for preparing optically active methionine in which acylated methionine is resolved with aminoacylase (Yakugaku Zasshi, 75, 113 (1955)); a method for preparing α-aminobutyric acid which comprises optically resolving acylated α-aminobutyric acid with acylase (Japanese Patent Laid-open No. 50-69009); and the like. However, these methods have also drawbacks that the substances to be resolved must disadvantageously be once acylated to give corresponding acylated derivatives and that use of enzymes which are derived from organism is inconvenient in handling from an industrial point of view.

Specific examples of the method (3) using optically active resolving agents are: a method for preparing optically active alanine in which benzoylalanine is treated with brucine or strychinine (J. Biol. Chem., 136, 355 (1940)); and methods for preparing methionine in which there is used a tartarate of methionine amide (Yakugaku Zasshi, 73, 357 (1953)); or a pyrrolidonecarboxylate of optically active methionine amide (Japanese Patent Publication No. 45-32250). This method using an optically active resolving agent is advantageous over the first two methods if the resolving agent is available inexpensively. However, since only a few resolving agents which are strongly acidic or strongly basic are known, most of substances to be resolved must undesirably be converted into derivatives, as indicated above, so as to yield diastereomers of the substances.

On the other hand, optical resolution of mandelic acid has been chiefly conducted, up to now, by a diastereomer method. A number of resolving agents including alkaloids, optically active amines, etc., are known for the above purpose but most of the agents are expensive, thus being unfavorable for the industrial production of the acid. It has been reported that L-mandelic acid can be optically resolved from DL-mandelic acid by means of L-phenylalanine (Nippon Kagaku Zasshi), 92, 999-1002 (1971)). To obtain useful D-mandelic acid, it is essential to use expensive D-phenylalanine, thus being unfavorable from an industrial standpoint. In the article, it is stated that the phenylalanine and mandelic acid are combined by a hydrophobic bond between their aromatic rings as well as by ion and hydrogen bonds and that the hydrophobic bond is an important factor for formation of the complexes.

Further, an attempt has been made to optically resolve DL-mandelic acid from an aqueous solution thereof adjusted to a pH of 5 by use of an L-methionine resolving agent but ended in failure (Kolloid-Z.Z. Polym., 215, 45 (1967)).

It is accordingly an object of the present invention to provide novel optically active amino acid-mandelic acid complexes which are useful for producing optically active amino acids or optically active mandelic acid.

It is another object of the present invention to provide a process for preparing optically active amino acid-mandelic acid complexes which overcomes the disadvantages of the prior methods.

It is a further object of the present invention to provide a process for preparing optically active amino acid-mandelic acid complexes which is simple in operation and conveniently feasible in an industrial sense.

It is a still further object of the present invention to provide a process for preparing optically active amino acid-mandelic acid complexes by direct interaction of amino acids and mandelic acid under specific reaction conditions.

It is an additional object of the present invention to provide a process for preparing optically active amino acids or optically active mandelic acid which is useful in various fields.

According to one aspect of the present invention, there are provided novel, optically active amino acid-mandelic acid complexes expressed by the following formula

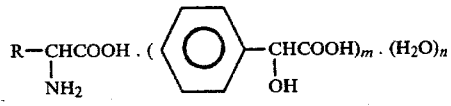

(in which R represents a methyl group, an ethyl group or a methylthioethyl group, m is 1 or 2, and n is 0 or ½).

Specific examples of the amino acids useful for preparing the complexes of the above formula according to the invention include methionine, alanine and α-aminobutyric acid though any amino acids as defined in the above formula may be used.

According to another aspect of the present invention, there is provided a process for preparing optically active amino acid-mandelic acid complexes of the formula as defined hereinabove, the process comprising interacting in a solvent under pH conditions of 1.0–4.0 an amino acid expressed by the following formula

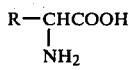

(in which R represents a methyl group, an ethyl group or a metylthioethyl group) and mandelic acid, one of the acids being an optically active substance and the other being a racemic modification, and resolving the resulting complexes by using a solubility difference therebetween to permit selective crystallization of a sparingly soluble one. The process of the present invention is based on a finding as a result of a series of our experiments that an amino acid such as alanine, methionine, α-aminobutyric acid or the like and mandelic acid are readily converted into complexes thereof in a solvent under conditions of a pH of 1.0–4.0. In other words, when DL-amino acid is treated with optically active mandelic acid, the amino acid is directly optically resolved under conditions as mentioned above. Similarly, when DL-mandelic acid is treated with an optically active amino acid, the mandelic acid is optically resolved.

According to a further aspect of the present invention, the complexes thus obtained can readily be separated into the amino acid and mandelic acid by a suitable means which will be described hereinafter, thereby obtaining optically active amino acid or mandelic acid.

The present invention will now be described in more detail.

In the preparation of the complexes according to the invention, either an DL-amino acid is treated with an optically active mandelic acid or DL-mandelic acid is treated with an optically active amino acid in solvent in either case to form complexes thereof.

Then, the solution is cooled or condensed, if necessary, or mixed with a solvent capable of reducing the solubility of one of the complexes thereby permitting selective crystallization of a more sparingly soluble complex to obtain crystals of the complex by a solid-liquid separation.

In the crystallization, addition of seed crystals is not necessarily required but a very small amount of the sparingly soluble complex may be added to facilitate the crystallization.

The substance to be resolved may be an equimolar mixture of a D-isomer and an L-isomer or may be a mixture which contains one of the optical isomers in greater amount by mole than its antipode.

Any solvents may be used for the practice of the invention if they can dissolve sparingly soluble and readily soluble complexes at temperatures between room temperature and a boiling point of solvent and permit selective crystallization of the sparingly soluble complex by cooling, condensation or addition of other solvents. Preferably, water or mixtures of water and hydrophilic organic solvents such as methanol, ethanol, acetone, etc., are used.

The reaction temperature is generally in the range between the boiling point of a solvent used and 0° C., preferably in the range between the boiling point and 50° C. The pH of the reaction system is preferred to be in the range of 1.0–4.0.

Any temperature below the boiling point of the solvent used may be used for the crystallization without limitation and it is preferred to be in the range of 0° C. to 50° C.

The molar ratio of amino acid to mandelic acid is in the range of 1:0.3–6.0, preferably 1:1.0–5.0. The concentration of amino acid in the chosen solvent is generally in a relatively wide range of 10–70 wt% though it may vary depending on the kind of amino acid.

The optically active complexes obtained according to the invention may be recrystallized by any technique known to the art if they are not pure optically.

Various complexes prepared by the practice of the invention are shown in the following table together with their physical properties such as melting point, specific rotatory power and solubilities in water.

TABLE 1

| Complex | Molar Ratio | | | Elementary Analysis | | | | | | $[\alpha]_D^{25}$ (C = 2.4, water) | Melting point | Solubilities in water | |
| | mandelic acid | amino acid | water | calculated | | | found | | | | | 10° C. wt % | 30° C. wt % |
| | | | | C% | H% | N% | C% | H% | N% | | | | |
| L-Ala . L-MA | 1 | 1 | — | 54.76 | 6.26 | 5.81 | 54.95 | 6.14 | 5.74 | +94.08° | | 14.15 | 23.92 |
| D-Ala . D-MA | 1 | 1 | — | 54.76 | 6.26 | 5.81 | 54.89 | 6.18 | 5.79 | −96.41 | | 14.30 | 23.84 |
| D-Ala . L-MA . ½ hydrate | 1 | 1 | ½ | 52.80 | 6.44 | 5.60 | 52.76 | 6.41 | 5.56 | +87.23 | | 8.18 | 14.63 |
| L-Ala . D-MA . ½ hydrate | 1 | 1 | ½ | 52.80 | 6.44 | 5.60 | 52.86 | 6.43 | 5.47 | −86.21 | | 8.37 | 14.30 |
| L-Met . L-MA | 2 | 1 | — | 58.65 | 5.72 | 1.85 | 58.52 | 5.68 | 1.80 | +101.74 | Showing | 5.52 | 13.35 |
| D-Met . D-MA | 2 | 1 | — | 58.65 | 5.72 | 1.85 | 58.44 | 5.64 | 1.78 | −102.55 | no | 6.03 | 13.37 |
| D-Met . L-MA | 1 | 1 | — | 51.81 | 6.36 | 4.65 | 51.76 | 6.35 | 4.63 | +75.12 | distinctive | 7.61 | 12.79 |
| L-Met . D-MA | 1 | 1 | — | 51.81 | 6.36 | 4.65 | 51.79 | 6.34 | 4.53 | −74.47 | melting | 7.82 | 12.93 |
| L-ABA . L-MA | 1 | 1 | — | 56.46 | 6.72 | 5.49 | 56.43 | 6.73 | 5.43 | +91.17 | point | 16.13 | 41.11 |
| D-ABA . D-MA | 1 | 1 | — | 56.46 | 6.72 | 5.49 | 56.39 | 6.67 | 5.46 | −91.25 | | 16.25 | 41.08 |
| D-ABA . L-MA . ½ hydrate | 1 | 1 | ½ | 52.74 | 7.01 | 5.12 | 52.91 | 6.93 | 5.17 | +80.84 | | 15.90 | 27.30 |
| L-ABA . D-MA . ½ hydrate | 1 | 1 | ½ | 52.74 | 7.01 | 5.12 | 52.80 | 6.90 | 5.08 | −80.23 | | 15.87 | 27.36 |

Note:
MA: mandelic acid
Met: methionine
Ala: alanine
ABA: α-aminobutyric acid

To obtain optically active amino acid or mandelic acid, the complex may be further treated, after being dissolved in water or a water-containing organic solvent: (1) The complex is decomposed by a mineral acid and the resulting mandelic acid is separated with use of an organic solvent (e.g., ether); or (2) The complex is separated into amino acid and mandelic acid by use of a weakly basic ion-exchange resin or a strongly acidic ion-exchange resin. Examples of the mineral acids are hydrochloric acid, sulfuric acid and the like. Typical of the weakly basic ion-exchange resin are, for example, styrene-divinylbenzene copolymer introduced with an amine, acrylic resin, phenolic resin, epoxy resin and the like. Typical of the strongly acidic ion-exchange resin is a styrene-divinylbenzene copolymer having sulfonic acid groups.

The optically active amino acids thus obtained have practical utility, e.g., L-alanine is useful as a food additive, L-n-α-aminobutyric acid is a starting material for preparing ethanebutol useful as an anti-tuberculotic agent, and L-methionine is very important as one component of amino acid transfusion.

Optically active mandelic acid isomers are also useful: the L-isomer is important as an agent capable of producing salts by reaction with various medical substances; and the D-isomer is important as a starting material for preparing synthetic cephalosporins.

The optically active amino acids or optically active mandelic acid used as a resolving agent may be repeatedly used.

The process of the present invention has several advantages over conventional processes, which follow.

1. There is no need of converting the amino acid to be resolved into a derivative thereof.
2. Water can be conveniently used as solvent.
3. Since one of the compounds forming the complex is used as a resolving agent to optically resolve the other compound, an intended, optically active substance can be obtained in the same apparatus and procedure as the complex.

The present invention will be particularly illustrated by way of the following examples.

EXAMPLE 1

3.56 g of L-alanine and 6.08 g of DL-mandelic acid were admixed with 10 ml of water and heated for dissolution (pH 3.44 at 40° C.), followed by allowing to stand at room temperature for 2 hours. The precipitated crystals were separated by filtration, washed with 4 ml of water, and dried to obtain 5.80 g of crude crystals of L-alanine.D-mandelic acid.½ hydrate. The thus obtained complex had a specific rotatory power of $[\alpha]_D^{25} = -72.3°$ (C=2.4, water). 5.00 g of the crude crystals were recrystallized from 5.0 ml of water to obtain 2.61 g of pure crystals with $[\alpha]_D^{25} = -84.2°$ (C=2.4, water). Since optically pure L-alanine.D-mandelic acid.½ hydrate was known to have a specific rotatory power, $[\alpha]_D^{25} = -86.2°$ (C=2.4, water), the optical purity was 98%.

EXAMPLES 2–5

Several kinds of optically active amino acids were used and optically resolved with DL-mandelic acids in the same manner as in Example 1. The test results are shown in Table 1 below.

TABLE 2

| Example No. | Amino Acid gr. | DL-mandelic acid gr. | Water ml | Crude Crystals yield gr. | Crude Crystals $[\alpha]_D^{25°}$ (C = 2.4, water) | Pure Crystals yield gr. | Pure Crystals $[\alpha]_D^{25°}$ (C = 2.4, water) | Composition of crystals Obtained |
|---|---|---|---|---|---|---|---|---|
| 2 | L-Met 2.98 | 6.09 | 8.5 | 1.77 | −60.2 | 1.24 | −72.8 | L-Met . D-MA |
| 3 | D-Met 2.98 | 6.09 | 8.5 | 1.86 | +58.4 | 1.26 | +72.3 | D-Met . L-MA |
| 4 | D-Ala 1.78 | 3.04 | 5.0 | 2.76 | +73.2 | 2.05 | +85.2 | D-Ala . L-MA . ½ hydrate |
| 5 | L-ABA 4.12 | 6.09 | 6.0 | 4.03 | −79.5 | | | L-ABA . D-MA . ½ hydrate |

EXAMPLE 6

4.12 g of DL-α-aminobutyric acid and 6.09 g of D-mandelic acid were admixed with 6 ml of water and heated for dissolution (pH 3.50 at 56° C.), and then allowed to stand at room temperature for 1 hour. The resulting crystals were separated by filtration, washed with 3.0 ml of water and dried to obtain 4.40 g of crystals of L-α-aminobutyric acid.D-mandelic acid.½ hydrate. The crystals had $[\alpha]_D^{25} = -80.4°$ (C=2.4, water).

EXAMPLES 7–11

Several kinds of DL-amino acids were optically resolved by the action of optically active mandelic acid used as a resolving agent in the same manner as in Example 6 with the results of Table 2 shown below.

With regard to alanine and methionine, the crude crystals were purified in the same manner as in Example 1 to give pure crystals, and the pure crystals were tested to determine a specific rotatory power as indicated in the Table.

TABLE 3

| Example No. | Mandelic Acid | Amino Acid Kind | Amino Acid gr. | Water ml | Crude Crystals gr. | Crude Crystals $[\alpha]_D^{25°}$ (C = 2.4, water) | Pure Crystals gr. | Pure Crystals $[\alpha]_D^{25°}$ (C = 2.4, water) | Composition of Crystals Obtained |
|---|---|---|---|---|---|---|---|---|---|
| 7 | D-6.09 | DL-Met | 1.49 | 18.0 | 2.67 | −133.2 | 2.40 | −102.5 | D-Met . 2 D-MA |
| 8 | L-6.09 | DL-Met | 1.70 | 18.0 | 2.70 | +127.8 | 2.50 | +101.7 | L-Met . 2 L-MA |
| 9 | D-6.09 | DL-Ala | 3.56 | 10.0 | 5.50 | −73.4 | 4.20 | −84.5 | L-Ala . D-MA . ½ hydrate |
| 10 | L-6.09 | DL-Ala | 3.56 | 10.0 | 5.30 | +72.5 | 4.15 | +84.8 | D-Ala . L MA . ½ hydrate |
| 11 | L-6.09 | DL-ABA | 4.12 | 6.0 | 4.20 | +78.4 | — | — | D-ABA . L-MA . ½ hydrate |

EXAMPLE 12

2.97 g of L-alanine and 7.61 g of DL-mandelic acid were dissolved in 25 ml of an aqueous 50 vol% methanol solution under heating conditions (pH 3.74 at 51° C.), allowed to stand at room temperature for 2 hours, and then filtered to obtain 3.92 g of crude crystals of L-alanine.D-mandelic acid ½ hydrate with $[\alpha]_D^{25} = -77.5°$ (C=2.4, water). The crude crystals were recrystallized from an aqueous 50 vol% methanol solution to obtain 3.12 g of pure crystals with $[\alpha]_D^{25} = -84.3°$ (C=2.4, water)

EXAMPLE 13

2.97 g of L-alanine and 7.61 g of DL-mandelic acid were admixed with 15 ml of an aqueous 33.3 vol% ethanol solution (i.e., water:ethanol=2:1) and heated for dissolution (pH 3.51 at 38° C.), followed by allowing to stand at room temperature for 3 hours and filtering to obtain 4.20 g of crude crystals of L-alanine.D-mandelic acid.½ hydrate. The crude crystals were found to have $[\alpha]_D^{25} = -54.8°$ (C=2.4, water). The crude crystals were recrystallized from 5 ml of an aqueous 33.3 vol% ethanol solution to obtain 2.51 g of pure crystals with $[\alpha]_D^{25} = -83.8°$ (C=2.4, water).

EXAMPLE 14

1.2 g of DL-α-aminobutyric acid and 2.85 g of L-mandelic acid were dissolved under heating in 5 ml of an aqueous 50 vol% ethanol solution (pH 3.55 at 44° C.), which was cooled in iced water and filtered to obtain 0.40 g of crude crystals of D-α-aminobutyric acid.L-mandelic acid.½ hydrate. The crystals had $[\alpha]_D^{24.7} = +80.25°$ (C=2.4, water). The crystals were so high in optical purity that no recrystallization was needed.

EXAMPLE 15

2.49 g of L-methionine and 5.07 g of DL-mandelic acid were dissolved under heating conditions in an aqueous 33.3 vol% ethanol solution (pH 3.39 at 63° C.). The solution was allowed to stand at room temperature for 1 hour and filtered to obtain 1.63 g of crude crystals of L-methionine.D-mandelic acid with $[\alpha]_D^{25.0} = -68.6°$ (C=2.4, water). The crude crystals were recrystallized from 2 ml of an aqueous 33.3 vol% ethanol solution to obtain 1.34 g of pure crystals with $[\alpha]_D^{25.0} = -73.5°$ (C=2.4, water).

EXAMPLE 16

2.50 g of the pure crystals obtained in Example 1 was dissolved in 10 ml of water at room temperature and the solution was passed through 20 ml of Dowex 50 W X-4 (H type)® (i.e., styrene.divinylbenzene copolymer having sulfonic acid groups, product of Dow Chem. Co.), followed by washing. 200 ml of the effluent was concentrated under reduced pressure and evaporated to dryness to obtain 1.49 g of D-mandelic acid with $[\alpha]_D^{25} = -153.4°$ (C=2.4, water).

EXAMPLE 17

1.00 g of the pure crystals obtained in Example 2 was dissolved in 1.5 ml of 10% hydrochloric acid and the solution was placed in a separating funnel in which D-mandelic acid was extracted with 2 ml of ether three times. The extract solution was evaporated to dryness to obtain 0.49 g of D-mendelic acid with $[\alpha]_D^{25} = -152.9°$ (C=2.4, water).

EXAMPLE 18

4.00 g of the crude crystals obtained in Example 6 was dissolved in 10 ml of water and the solution was passed through 23 ml of Dowex 50W X-4 (H type)®, followed by washing sufficiently and then eluting or dissolving out with 15 ml of aqueous 14% ammonia. 200 ml of the eluent was concentrated under reduced pressure and evaporated to dryness to obtain 1.60 g of L-α-aminobutyric acid with $[\alpha]_D^{25} = +19.2°$ (C=4.9, 6 N HCl).

EXAMPLE 19

3.90 g of the pure crystals obtained in Example 9 was dissolved in 45 ml of water at room temperature and the solution was passed through 16 ml of Diaion WA-20® (i.e., styrene.divinylbenzene copolymer with amine group, product of Mitsubishi Chem. Ind., Co.) followed by washing. 70 ml of the effluent collected was condensed under reduced pressure and evaporated to dryness to obtain 1.36 g of L-alanine with $[\alpha]_D^{20} = +14.7°$ (C=10, 6 N HCl).

What is claimed is:

1. A process for preparing an optically active amino acid-mandelic acid complex characterized by reacting in a solvent, at a pH of 1.0 to 4.0 and at a temperature of room 50° C. to the boiling point of the solvent, an optically active isomer of an amino acid of the formula:

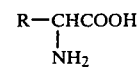

wherein R is a methyl, ethyl or methylthioethyl group, with racemic mandelic acid in an amount of 0.3 to 6.0 equivalents per unit equivalent to said amino acid, or a raceme of said amino acid with an optically active isomer of mandelic acid in an amount of 0.3 to 6.0 equivalents per unit equivalent to said amino acid, and crystallizing and separating the thus resulting complexes by selective crystallization of the less soluble isomer complex at a temperature of from 0° to 50° C.

2. A process according to claim 1, wherein said solvent is a member selected from the group consisting of water, water-containing methanol, water-containing ethanol and water-containing acetone.

3. A process according to claim 1, wherein the concentration of said amino acid is 10–70% by weight of said solvent.

4. A process for preparing an optically active substance of the formula:

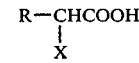

wherein X is an amino group and R is a methyl, ethyl or methylthioethyl group, or X is hydroxy group and R is phenyl group; which process comprises reacting in a solvent, at a pH of 1.0 to 4.0 and at a temperature of from 50° C. to the boiling point of the solvent, an optically active isomer of an amino acid of the formula:

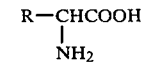

wherein R is a methyl, ethyl or methylthioethyl group, with racemic mandelic acid in an amount of 0.3 to 6.0 equivalents per unit equivalent to said amino acid, or a raceme of said amino acid with an optically active isomer of mandelic acid in an amount of 0.3 to 6.0 equivalents per unit equivalent to said amino acid, crystallizing and separating the thus resulting complexes by selective crystallization, at a temperature of from 0° to 50° C., and decomposing each of the two crystallized optically active complexes thus resolved by adding an acid, a strongly acidic ion-exchange resin or a weak basic ion-exchange resin.

5. A process according to claim 4, wherein said solvent is a member selected from the group consisting of water, water-containing methanol, water-containing ethanol and water-containing acetone.

6. A process according to claim 4, wherein the concentration of said amino acid is in the range of 10–70% by weight of said solvent.

7. A process according to claim 4, wherein said acid is hydrochloric acid or sulfuric acid.

8. A process according to claim 4, wherein said strongly acidic ion-exchange resin is a styrene.divinylbenzene copolymer introduced with sulfonic acid groups.

9. A process according to claim 4, wherein said weakly basic ion-exchange resin is a styrene.divinylbenzene copolymer introduced with amine, acrylic resin, phenolic resin or epoxy resin.

* * * * *

UNITED STATES PATENT AND TRADEMARK OFFICE
CERTIFICATE OF CORRECTION

PATENT NO. : 4,224,239
DATED : September 23, 1980
INVENTOR(S) : Y. TASHIRO et al It is certified that error appears in the above-identified patent and that said Letters Patent are hereby corrected as shown below:

Claim 1, line 4, change "room" to --from--.

Signed and Sealed this

Second Day of June 1981

[SEAL]

Attest:

RENE D. TEGTMEYER

Attesting Officer     Acting Commissioner of Patents and Trademarks